US008828332B2

(12) United States Patent
Thorslund et al.

(10) Patent No.: US 8,828,332 B2
(45) Date of Patent: Sep. 9, 2014

(54) MICROFLUIDIC CAPSULE

(75) Inventors: Sara Thorslund, Uppsala (SE); Johan Kreuger, Uppsala (SE); Hugo Nguyen, Uppsala (SE)

(73) Assignee: Gradientech AB, Uppsala (SE)

( * ) Notice: Subject to any disclaimer, the term of this patent is extended or adjusted under 35 U.S.C. 154(b) by 0 days.

(21) Appl. No.: 13/821,293

(22) PCT Filed: Jun. 30, 2011

(86) PCT No.: PCT/SE2011/050884
§ 371 (c)(1),
(2), (4) Date: Mar. 7, 2013

(87) PCT Pub. No.: WO2012/033439
PCT Pub. Date: Mar. 15, 2012

(65) Prior Publication Data
US 2013/0164192 A1    Jun. 27, 2013

(30) Foreign Application Priority Data

Sep. 10, 2010 (SE) ...................... 1050936

(51) Int. Cl.
C12M 3/00 (2006.01)
B01L 3/00 (2006.01)
C12M 1/28 (2006.01)
B01L 9/00 (2006.01)
C12M 1/00 (2006.01)

(52) U.S. Cl.
USPC .............. 422/502; 435/287.2; 435/289.1; 435/283.1; 422/550; 422/554; 422/559

(58) Field of Classification Search
None
See application file for complete search history.

(56) References Cited

U.S. PATENT DOCUMENTS

| 2007/0125434 | A1 | 6/2007 | Nakao |
| 2008/0102478 | A1 | 5/2008 | Li et al. |
| 2008/0176253 | A1* | 7/2008 | Christodoulides et al. .. 435/7.21 |
| 2008/0194804 | A1 | 8/2008 | Chang et al. |
| 2008/0219890 | A1 | 9/2008 | Lawson et al. |
| 2011/0217771 | A1 | 9/2011 | Thorslund et al. |

FOREIGN PATENT DOCUMENTS

| AU | 2006335679 B2 | 7/2007 |
| WO | WO03087410 A1 | 10/2003 |
| WO | WO2008005998 A2 | 1/2008 |
| WO | WO2009126524 A2 | 10/2009 |

OTHER PUBLICATIONS

Zaytseva et al., Development of a Microfluidic Biosensor Module for Pathogen Detection, The Royal Society of Chemistry, Lab Chip, 2005, 5, pp. 805-811.

* cited by examiner

Primary Examiner — Dirk Bass
Assistant Examiner — Jennifer Wecker
(74) Attorney, Agent, or Firm — Porter Wright Morris & Arthur LLP

(57) ABSTRACT

A microfluidic capsule (1) comprises a top lid (100), a middle piece (200) and a bottom piece (300) to be assembled to enclose a microfluidic substrate (400) for analysis of cells and biochemical reactions. The middle piece (200) comprises support structures in the form of support pillars (250) and walls (240) around a central light window (220) to provide mechanical support and prevent tension-induced structural deformations. When fully assembled, light windows (120, 220, 230) in the top lid (100), middle piece (200) and bottom piece (300) allows inspection of biological and/or biochemical samples positioned in the enclosed microfluidic substrate (400).

16 Claims, 7 Drawing Sheets

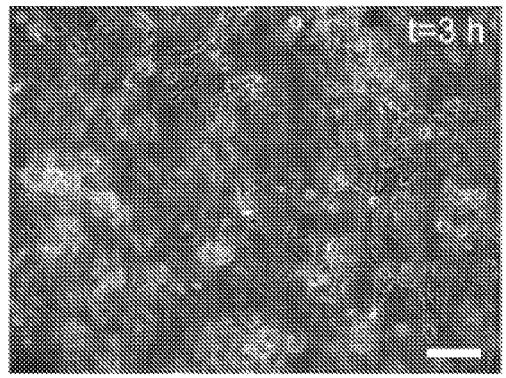 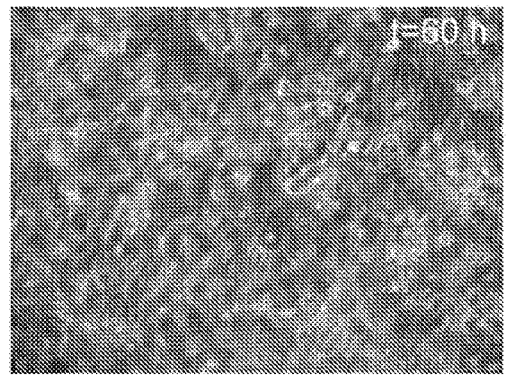
Fig. 9A  Fig. 9B
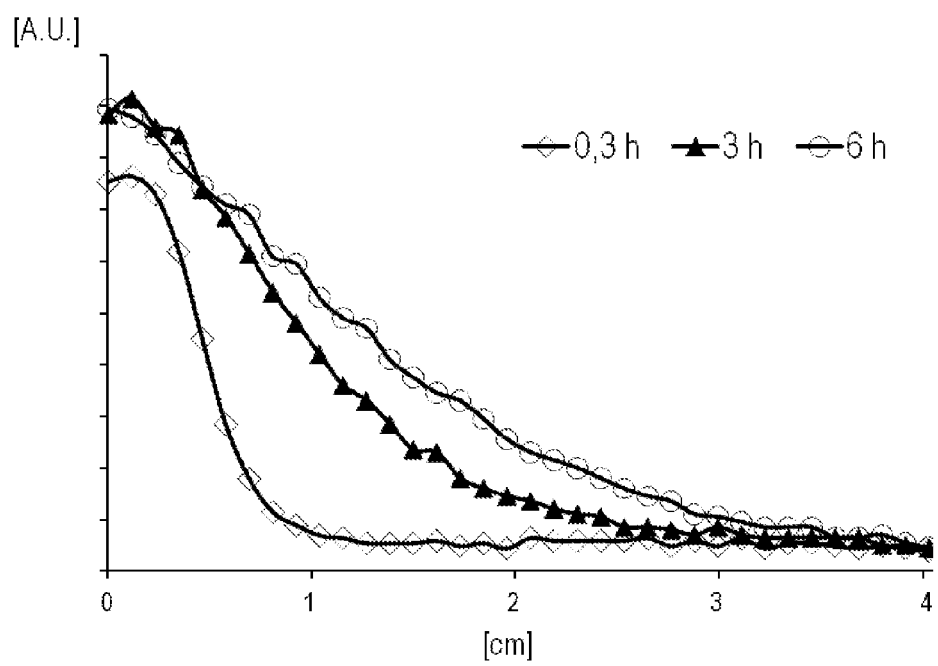
Fig. 10

MICROFLUIDIC CAPSULE

TECHNICAL FIELD

The present invention generally relates to microfluidic capsules, and in particular to such microfluidic capsules designed to house microfluidic substrates suitable for biochemical and/or cell culture experiments.

BACKGROUND

Microfluidic technology has the potential to revolutionize experimentation with living cells in vitro. Numerous studies providing proof-of-principle for novel high-quality cell assays based on microfluidics have been published over the past decade. A good set of examples of what microfluidics has to offer modern biology are the increasing number of assays designed to allow formation of predictable concentration gradients in different cell culture setups. Concentration gradients of signaling molecules are central to cell-cell communication in all multicellular organisms. In many of the microfluidic cell culture systems, the fluidic channels and the cavities for cell culture are created in polydimethylsiloxane (PDMS) sealed by bonding to a glass surface. These assays enable real-time studies of cell migration, proliferation and differentiation in response to concentration gradients of soluble signaling molecules (often proteins), in both two- and three-dimensional settings. Conceivably, some of these new methods based on microfluidic technology could become new global standards, and thereby in part replace techniques such as, for example, the Boyden chamber assay for the study of chemotaxis.

The market for microfluidic cell assays and applications has considerable growth potential. This is in part propelled by the need for new in vitro systems in academic research to better replicate biological processes, but also because of an increasing demand from regulatory authorities for improved cell-based screening of chemical compounds in the process of drug development. However, in spite of the great promise of microfluidics to both improve and accelerate biological research, the commercial impact so far is small.

A main reason for the modest use of microfluidics in various cell culture applications is likely that most microfluidic assays of today are fairly difficult to set up and operate for non-expert users. There is however a growing body of simplistic and commercially available systems, and several companies such as BellBrook Labs (WI, USA), Xona Microfluidics LLC (CA, USA) and Ibidi GmbH (Germany) have fluidic devices for cell studies on sale.

US 2008/0194804 discloses a microfluidic chip-based hybridization device. The device consists of an upper basal plate, a lower basal plate and a substrate that are stacked together. The upper basal plate has a hybridization region in which the substrate is positioned. A central inlet/outlet hole runs through the middle of the hybridization region, which is further connected to a microfluidic channel that is linked to another inlet/outlet hole.

US 2007/0125434 relates to a microfluidic device capable of preventing the flow of fluid from being interrupted by bubbles generated in a micro flow passage. A narrow portion of the micro flow passage is formed by arranging a columnar portion in the micro flow passage. The bubble trapping means is a recessed portion which is formed in an upper surface of the micro flow passage upstream of the columnar portion.

US 2008/0102478 discloses a polymeric chip having multiple three-dimensional porous scaffolds, a microfluidic channel inlet to the porous scaffold and a microfluidic channel outlet from the porous scaffold. The chip is designed to be used as a multi-organ tissue model system.

However, there is still a need for a versatile microfluidic capsule that enable easy assembly and operation of microfluidic substrates.

SUMMARY

It is a general objective to provide a microfluidic capsule to be used in connection with microfluidic substrates for biochemical and/or cell culture analysis.

It is a particular objective to provide such a microfluidic capsule with improved structural integrity and reduced risk for tension-induced structural deformations during and after assembly.

These and other objectives are met by the embodiments as disclosed herein.

Briefly, a microfluidic capsule comprises three main components in the form of a top lid, a middle piece and a bottom piece. The top lid is in the form of a lid sheet comprising a light window. The middle piece comprises a middle sheet comprising at least one fluid inlet and at least one fluid outlet and a light window. The light window has a circumferential or circumferentially distributed wall around its perimeter. Multiple raised walls are circumferentially distributed around the perimeter of the middle sheet and are separated by raised connection structures that are to interact with snap-fit structures of the bottom piece during assembly. At least one support pillar is attached to the middle sheet and positioned between the perimeters of the middle sheet and the light window. The ends of the raised walls, the circumferential or circumferentially distributed wall and the at least one support pillar facing opposite to the middle sheet are arranged to be attached to the top lid. The support pillar and the circumferential or circumferentially distributed wall thereby provides structural support to reduce the risk of structural deformations of the middle sheet during assembly of the microfluidic capsule.

Inlet connector connects the fluid inlet to the outside of the microfluidic capsule by protruding through an opening in a wall of the middle piece.

The bottom piece comprises a bottom sheet having a light window allowing visual inspection through the light windows of the top lid, the middle piece and the bottom piece when these three capsule components are attached to each other. Multiple snap-fit structures are circumferentially distributed around the perimeter of the bottom sheet to be aligned with the raised connection structures of the middle piece to lock the bottom piece to the middle piece in a snap-fit manner.

A transparent cover sheet or slip is positioned in the bottom piece so that a microfluidic substrate is positioned and sandwiched between the middle piece and the cover sheet to thereby enclose the microfluidic substrate, and align a culture chamber of the microfluidic substrate with the light windows and connect the fluid inlet and outlet with fluid channels of the microfluidic substrate. The open culture chamber and the fluid channels of the microfluidic substrate thereby become closed.

The microfluidic capsule allows an efficient handling of microfluidic substrates for cell culture experiments and/or biochemical analysis but without unacceptable structural deformations to the capsule and the enclosed microfluidic substrate.

BRIEF DESCRIPTION OF THE DRAWINGS

The invention, together with further objects and advantages thereof, may best be understood by making reference to the following description taken together with the accompanying drawings, in which:

FIGS. 9A and 9B illustrates primary human endothelial cells cultured within a microfluidic capsule, according to an embodiment, fitted with a microfluidic elastomer substrate intended for cell culture experiments and monitored over time (3 h—FIG. 9A and 60 h—FIG. 9B);

FIG. 10 illustrates the formation of a FITC-dextran (40 kDa) concentration gradient in a 4 mm wide culture chamber of a microfluidic elastomer substrate intended for cell culture experiments filled with fibrin gel in a microfluidic capsule according to an embodiment.

DETAILED DESCRIPTION

Figure 1:
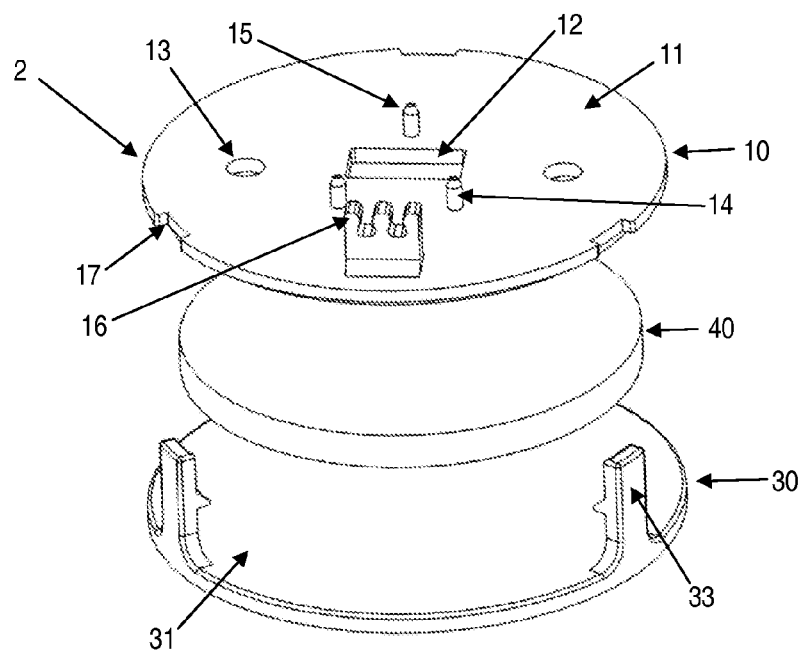
FIG. 1 is an exploded view of a prototype microfluidic capsule.

Throughout the drawings, the same reference numbers are used for similar or corresponding elements.

The embodiments generally relate to a microfluidic capsule designed for enclosing and housing a microfluidic substrate, and in particular a microfluidic elastomer substrate designed for cell culture experiments and/or biochemical analysis, also denoted microfluidic culture substrate or device in the art.

The microfluidic capsule has the objective of facilitating handling of the microfluidic substrate in particular allowing an efficient technique of connecting the microfluidic substrate to externals systems, for instance providing input and output fluid flows to a culture chamber of the microfluidic substrate.

The microfluidic capsules hitherto known are marred by various problems. For instance, some of them do not allow assembly and deassembly of the microfluidic capsule in order to retrieve any intact biological sample from the culture chamber of the enclosed microfluidic substrate following operation of the microfluidic substrate. Additionally, prior art microfluidic capsules can have problems in terms of tension-related structural deformations of the capsule parts following assembly. Hence, rigid and expensive capsule parts have to be designed, thereby increasing the cost for manufacturing each microfluidic capsule.

Embodiments as disclosed herein solve the above problems and in particular the problems of tension-related structural deformation. In order to facilitate understanding of the advantageous effects of the embodiments and problems that can occur in connection with microfluidic capsules and deformations, an analysis of a prototype microfluidic capsule not forming part of the embodiments first follows with reference to FIG. 1. This microfluidic capsule 2 consisted of two separate parts, an upper piece 10 and a bottom piece 30. The upper piece 10 and bottom piece 30 were designed to be placed on the two opposite sides of a microfluidic substrate 40 and to thereby provide interfaces required for the fluidic functions. The microfluidic capsule 2 was created in DurusWhite using PolyJet 3D printing (Digital Mechanics, Sweden), and used for assembly tests according to the setup in FIG. 1. The top piece 10 consisted of a lid sheet 11 having a central light window 12 allowing visual inspection into the culture chamber of the microfluidic substrate 40. The lid sheet 11 also had two fluid inlets 14 and a single fluid outlet 15 to which an external fluid pumping system can be connected. The fluid inlets 14 in turn guide the input fluid into fluid channels running besides the culture chamber of the microfluidic substrate 40 and meet at an outlet channel, which becomes connected to the fluid outlet 15. A tube holder 16 can be attached to the top sheet 11 in order to hold the tubes of the external fluid pumping system in correct position.

Through holes 13 allow visual inspection of the enclosed microfluidic substrate 40. The top sheet 11 additionally comprises three circumferentially distributed notches 17 in the perimeter. Matching snap-fit or gripping structures 33 are placed in connection with the perimeter of a bottom sheet 31 of the bottom piece 30 to thereby snap-fit lock to the notches 17 and lock the bottom piece 30 to the top piece 10. At this point the microfluidic substrate 40 becomes tightly squeezed and locked between the top piece 10 and the bottom piece 30.

Figure 2:
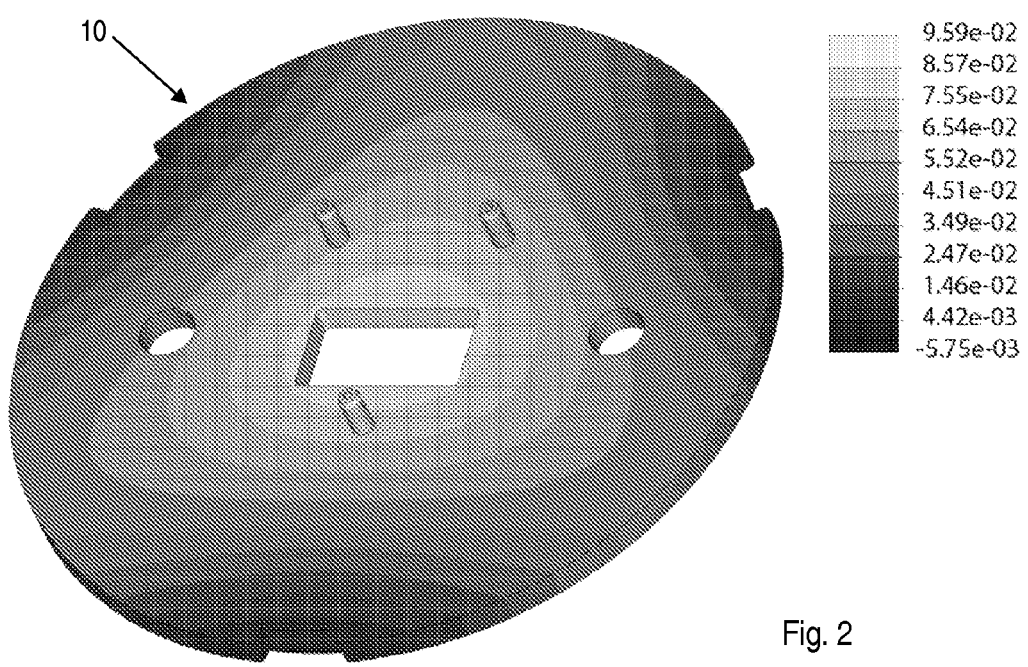
FIG. 2 depicts FEM modeling showing deformations in mm along the Z-axis in the upper piece of the prototype microfluidic capsule of FIG. 1.
Figure 3:
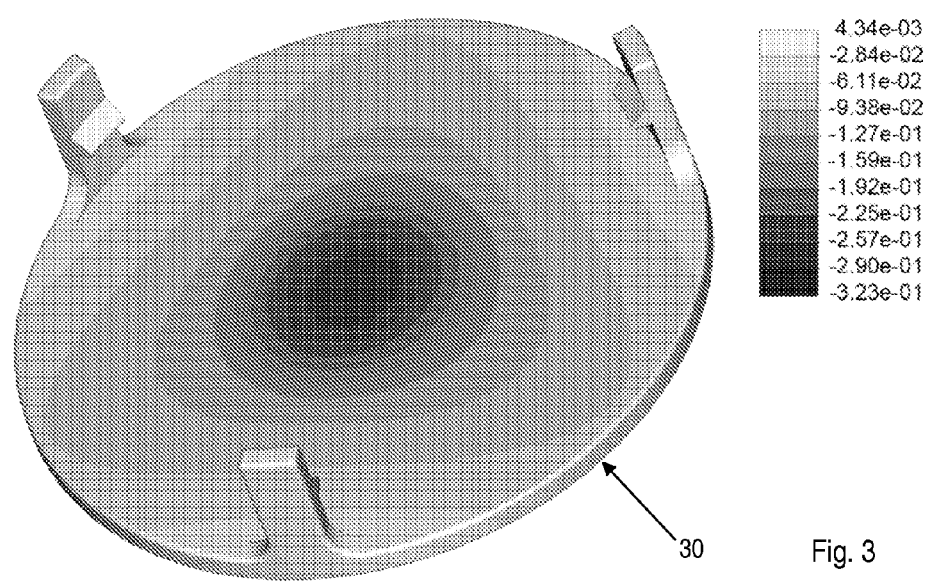
FIG. 3 depicts FEM modeling showing deformations in mm along the Z-axis in the bottom piece of the prototype microfluidic capsule of FIG. 1.

Test operation of the microfluidic capsule 2 of FIG. 1 showed that bending of the upper piece 10 upon assembly by snap-clamping of the microfluidic substrate 40 caused leakage from the fluidic channels. A structural finite element modeling (FEM) (material data for polystyrene: elasticity module=3 GPa, Poisson's ratio=0.4, ProMechanica software) was conducted, and revealed that the upper piece 10 acted as a membrane that did not resist the high pressure exerted from the clamped microfluidic substrate 40 (3 mm thick). The microfluidic substrate 40 could in this context be considered as a massive piece of an incompressible elastic material that provides even hydrostatic pressure upon clamping. A modest pressure of 10 kPa on the surface of the upper piece 10 (having a thickness of 1.5 mm) was by FEM analysis shown to induce bending of around 100 micrometers at the centre, see FIG. 2. An effective stress of 7.8 MPa was seen to be concentrated around the light window 12, whereas a stress around 2 MPa was detected in the solid part of the upper piece 10 for this pressure load. Similarly, significant bending of the bottom piece 30 was also shown to occur as a result of assembly, see FIG. 3. The 10 kPa pressure used here was taken from an iterative modeling and corresponded to a nominal 200 micrometers excess of the microfluidic substrate thickness.

An objective of the embodiments is therefore to provide a design and construction of a microfluidic capsule to counteract tension-related structural deformation in the capsule parts.

Figure 4:
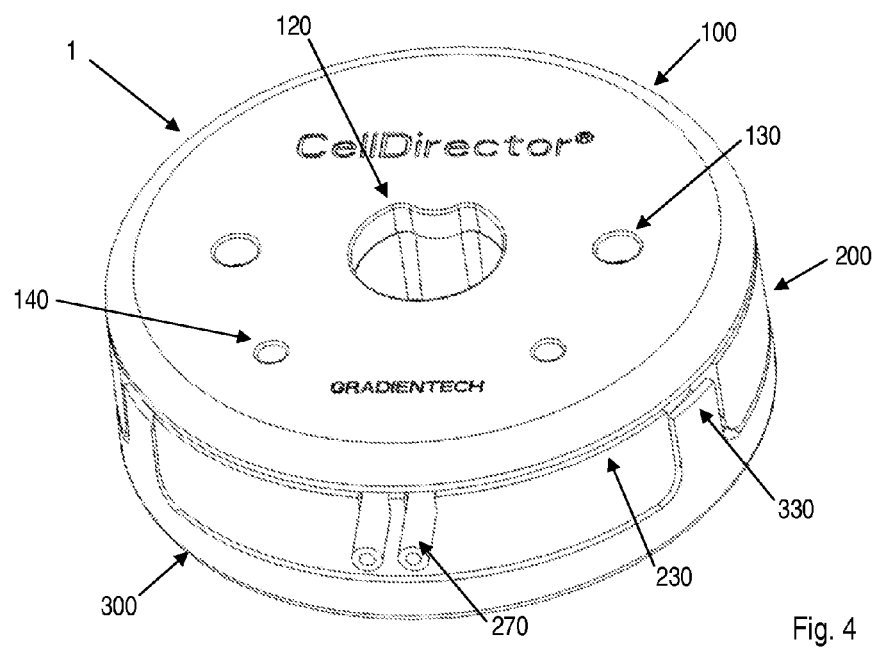
FIG. 4 is an imploded view of the fully assembled microfluidic capsule according to an embodiment.
Figure 5:
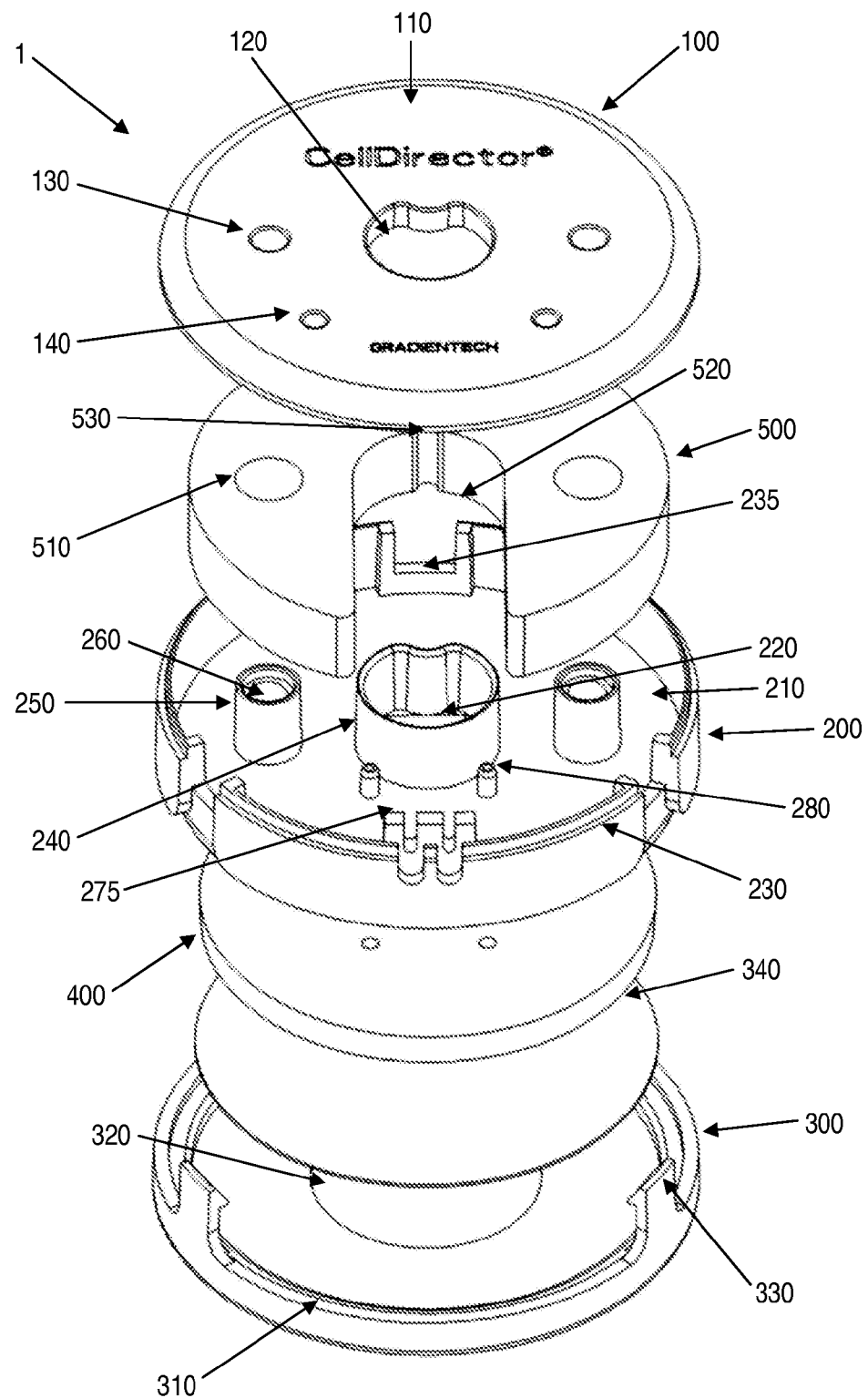
FIG. 5 is an exploded view of a microfluidic capsule according to an embodiment.
Figure 6:
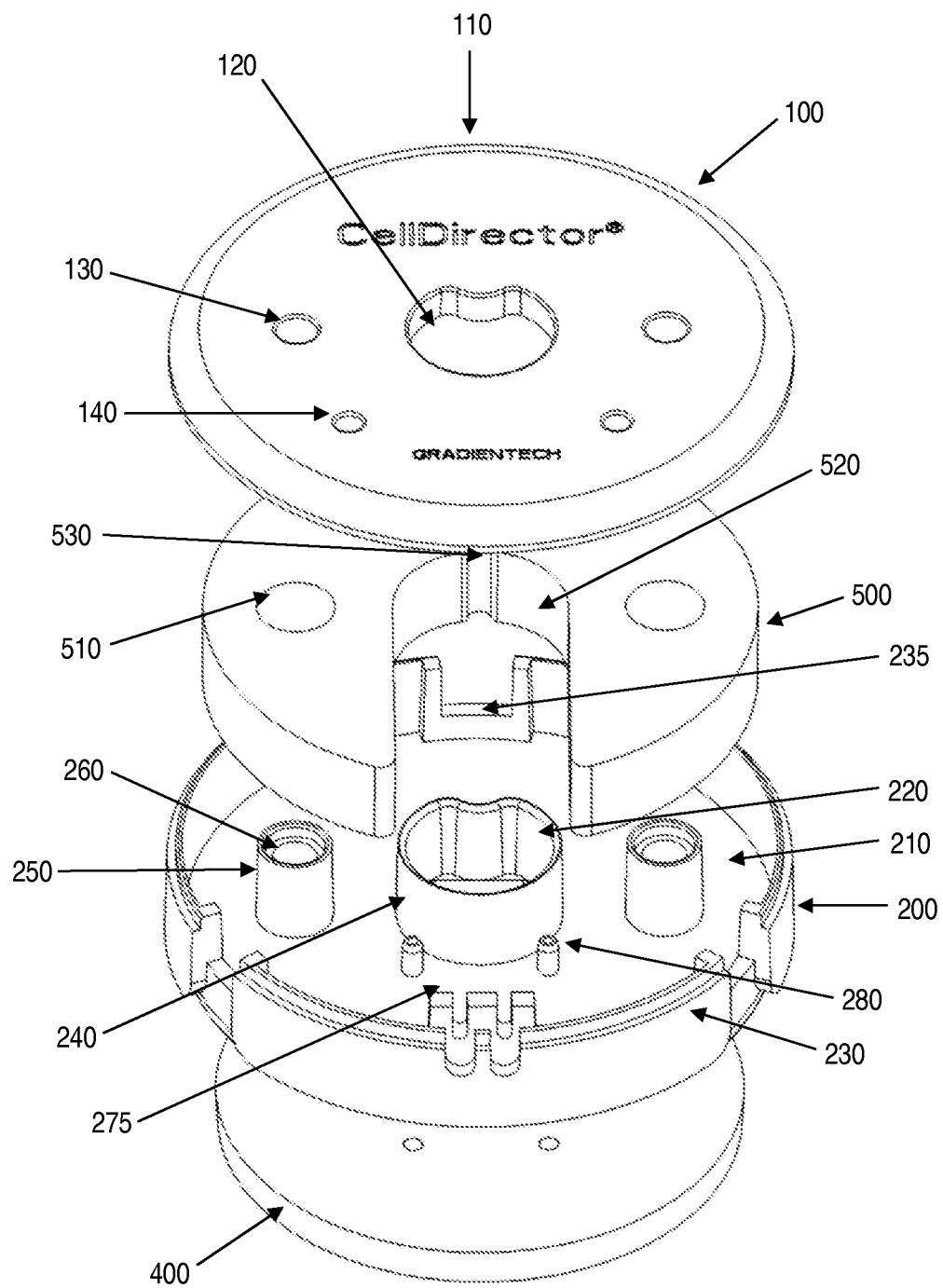
FIG. 6 is an exploded view of the upper unit of a microfluidic capsule according to an embodiment.

An embodiment of the microfluidic capsule 1 will now be described in more detailed in connection with FIGS. 4-6. FIG. 4 illustrates an imploded view of the fully assembled microfluidic capsule 1, FIG. 5 is an exploded view of a microfluidic capsule 1 and FIG. 6 is an exploded view of the upper unit of a microfluidic capsule 1.

The microfluidic capsule 1 comprises three main parts: a top lid 100, a middle piece 200 and a bottom piece 300 that are locked to each other during assembly as illustrated in FIG. 4.

The top lid 100 is in the form of a lid sheet 110 comprising a light window 120 typically, but not necessarily positioned in the centre of the lid sheet 110. This light window 120 allows, as is further described herein visual access, light access and gas exchange to a culture chamber of the microfluidic substrate 400 to be enclosed in the microfluidic capsule 1.

Figure 8:
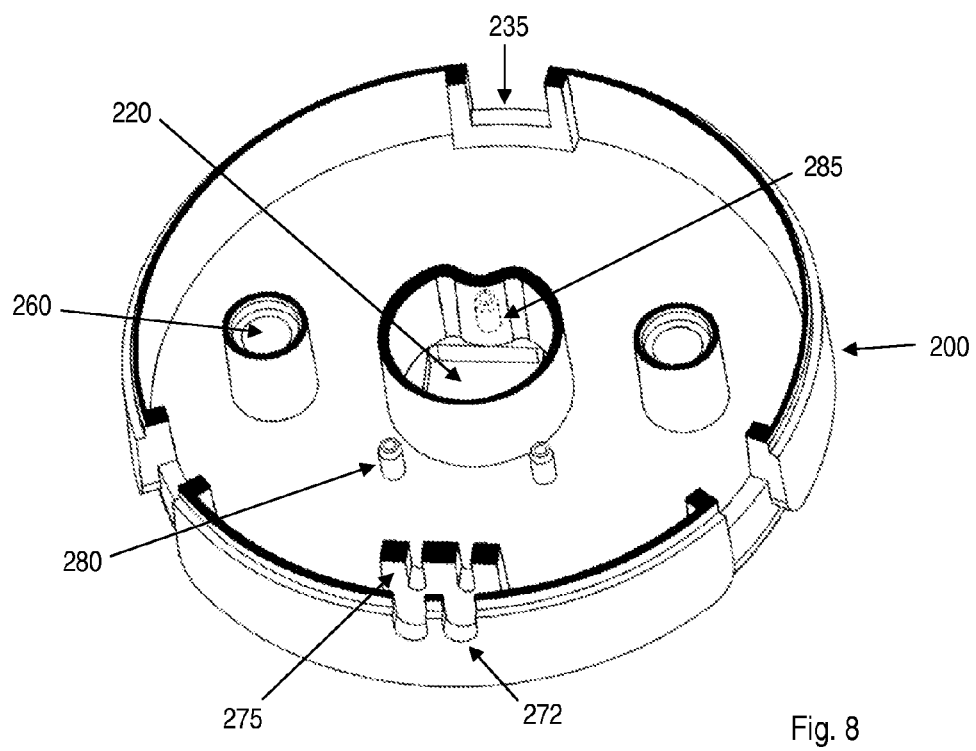
FIG. 8 schematically illustrates surfaces of the middle piece of the microfluidic capsule available for bonding to the top lid according to an embodiment.

The middle piece 200 comprises a middle sheet 210 comprising at least one fluid inlet 280 and at least one fluid outlet 285, see FIG. 8. In the figure, the middle piece 200 is illustrated as comprising two fluid inlets 280 to thereby be connected to respective fluid channels of the microfluidic substrate 400. In a typical embodiment, the middle piece 200 comprises one such fluid inlet 280 per fluid channel of the microfluidic device 400. In addition, the at least one fluid inlet 280 is positioned in the middle sheet 210 to be connected to the at least one fluid channel of the microfluidic substrate 400 when the microfluidic capsule 1 is closed as illustrated in FIG. 4. The at least one fluid outlet 285 is not visible in FIGS. 4-6 but is arranged on the opposite side of the wall 240 around a light window 220 as compared to the fluid inlet(s) 280, see FIG. 8. The at least one fluid outlet 285 is positioned in the middle sheet 210 to become aligned and connected with a respective fluid outlet of the microfluidic substrate 400 when the microfluidic capsule 1 is fully assembled.

In a particular embodiment, the fluid inlet(s) 280 and outlet(s) 285 are in the form of through holes in the middle sheet 210.

The middle sheet 210 also comprises a light window 220 positioned to be aligned with the light window 120 of the top lid 100 when the top lid 100 is attached to the middle piece 200 as illustrated in FIG. 4. This light window 220 further has a circumferential or circumferentially distributed wall 240 around its perimeter. In a first embodiment and as illustrated in FIGS. 5 and 6 the wall 240 extends around the complete perimeter of the light window 220, i.e. is a single continuous wall structure. In an alternative embodiment the wall 240 consists of multiple separate wall structures circumferentially distributed around the perimeter of the light window 240. Thus, in such a case there are gaps between the separate wall structures.

The middle piece 200 also comprises multiple raised walls 230 circumferentially distributed around the perimeter of the middle sheet 210. In FIGS. 4-6 three such raised walls 230 have been illustrated. This should, however, merely be seen as an illustrative example and the middle piece 200 could instead comprise two, four, five or even more raised walls 230. Each raised wall 230 could cover substantially a same portion or length of the perimeter of the middle sheet 210 as the other raised walls. This is, though, not necessary and raised walls 230 covering different lengths of the perimeter are also possible and within the scope of the embodiments.

The multiple raised walls 230 are separated from the neighboring or adjacent raised wall(s) by raised connection structures 235. These raised connection structures 235 have a height relative the middle sheet 210 that is lower than the height of the multiple raised walls 230 relative the middle sheet 210. Thus, the raised walls 230 extend past the raised connection structures 235, which are clearly seen in FIGS. 5 and 6.

The middle piece 200 comprises at least one support pillar 250 attached to or forming part of the middle sheet 210 at a position between the perimeter of the middle sheet 210 and the perimeter of the light window 220. The middle piece 200 could comprise a single support 250 or multiple such support pillars 250, e.g. two as illustrated in FIGS. 5 and 6. If the middle piece 200 comprises multiple support pillars 250 they are advantageously evenly distributed around the central light window 220.

The ends of the multiple raised walls 230, the wall 240 around the light window 220 and the at least one support pillar 250 facing opposite to the middle sheet 210 are arranged to be attached to the top lid 100. These structures therefore preferably have the same or similar heights relative the middle sheet 210. The oppositely facing ends are marked in black in FIG. 8. These ends can be attached to the top lid 100 according to various embodiments and depending on the particular material selected for the top lid 100 and the middle piece 200. Non-limiting examples include gluing and welding, in particular ultrasonic welding, between the ends and the corresponding portions of the bottom surface of the top lid 100.

The inclusion of the circumferential or circumferentially distributed walls 240 and the at least one support pillar 250 significantly improves the stability of the assembled microfluidic capsule 1 and significantly reduces any tension-related structural deformations, which is further described herein.

At least one inlet connector 270, such as in the form of a tube, is connected to the at least one fluid inlet 280. The tube therefore has a first end connected to a fluid inlet 280 and has a second, opposite end protruding through an opening 272 (see FIG. 8) in a wall of the multiple raised walls 230. In a particular embodiment, there is a one-to-one relationship between the numbers of inlet connectors 270 and the number of fluid inlets 280. Thus, the inlet connector 270 then has a respective tube for each fluid inlet 280. In an alternative embodiment, the inlet connector 270 can be in the form of a branched tube having a single end protruding through the opening 272 in a raised wall but branches off into multiple tube ends that are connected to a respective fluid inlet 280.

The bottom piece 300 comprises a bottom sheet 310 having a light window 320 positioned in the bottom sheet 310 to allow visual inspection through the light windows 120, 220, 320 of the top lid 100, the middle piece 200 and the bottom piece 300 when the bottom piece 300 is attached to the middle piece 200 and the top lid 100. Microscopy is enabled with the objective placed under the bottom piece 300 through the light window 320 and a transparent cover sheet 340.

The bottom piece 300 also comprises multiple snap-fit structures 330 circumferentially distributed around the perimeter of the bottom sheet 310 and extending from the bottom sheet 310. These snap-fit structures 330 are further positioned to match the positions of the raised connection structures 235 of the middle piece 200. Hence, the snap-fit structures 330 are aligned with the raised connection structures 235 and lock the bottom piece 300 to the middle piece 200 in a snap-fit manner by gripping the raised connection structures 235.

The three main parts of the microfluidic capsule 1 thereby becomes assembled and locked to each other through the attachment between the ends of the raised walls 230, the wall 240 around the middle light window 220 and the support pillar(s) 250 and the bottom surface of the top lid 100 and between the snap-fit structures 330 and the raised connection structures 235.

A transparent cover sheet 340 is further included in the microfluidic capsule 1 and positioned on the upper surface of the bottom sheet 310. The microfluidic substrate 400 thereby becomes enclosed by the microfluidic capsule 1 by positioning the microfluidic substrate 400 between the bottom piece 300 and the middle piece 200 so that an open culture chamber of the microfluidic substrate 400, facing the bottom piece 300 and aligned with the light windows 120, 220, 320, becomes closed by the transparent cover sheet 340 to form a closed culture chamber.

Figure 7:
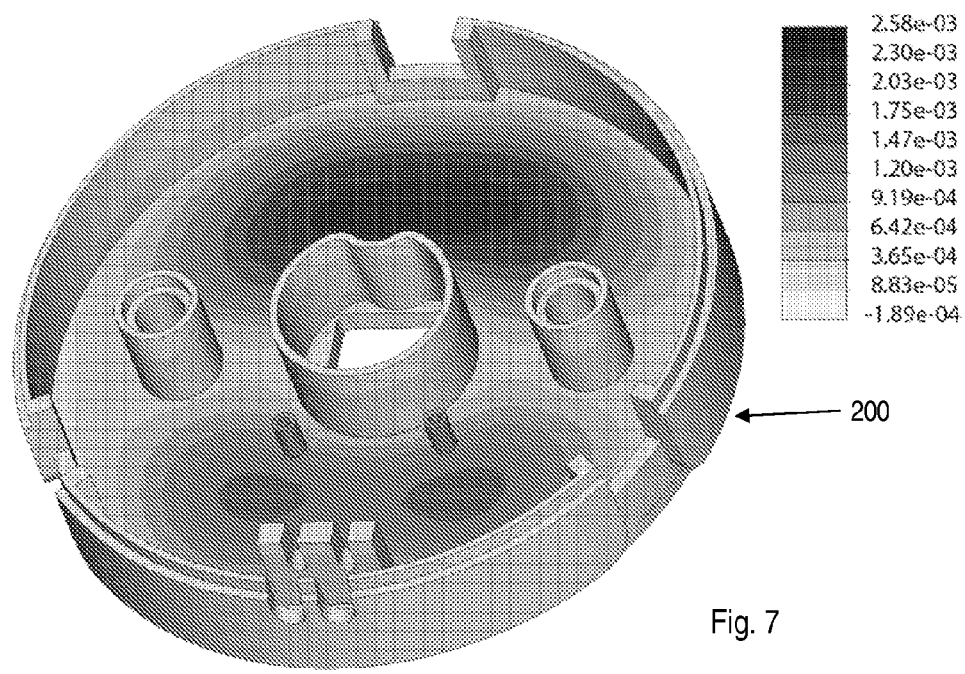
FIG. 7 depicts FEM modeling showing deformations in mm along the Z-axis in the middle piece of the microfluidic capsule of FIGS. 4-6.

The at least one support pillar 250 together with the circumferential or circumferentially distributed wall 240 and the raised walls 230 significantly stabilizes the fully assembled microfluidic capsule 1 and in particular reduces any tension-related structural deformations in three main parts of the capsule 1. In addition, the raised walls 230 together with the attachment of the top lid 100 made the upper unit illustrated in FIG. 6 and comprising the top lid 100 and the middle piece 200 mechanically robust and considerably enhanced the stiffness of the middle piece bottom surface. FIG. 7 illustrates FEM modeling of the middle piece 200 with structural components, i.e. support pillars 250, circumferential wall 240 around light window and raised walls 230 around outer perimeter, to counteract mechanical stress created by capsule assembly. The scale bar shows the deformation in mm along the z-axis. As can be seen in the figure, now a maximum bending of 3 micrometers occurred as compared to the capsule design of FIG. 1 with its FEM modeling illustrated in FIGS. 2 and 3.

The at least one support pillar 250 can have multiple different functions besides providing structural support and reducing any bending and structural deformations of the assembled microfluidic capsule 1. In a particular embodiment, the at least one support pillar 250 is at least one hollow support pillar 250 having a respective bore 260. In such a case, the top lid 100 comprises respective through hole(s) 130 positioned in the lid sheet 110 to be aligned with the respective bore(s) 260 when the top lid 100 is attached to the middle piece 200. In such a case, visual inspection is possible from the top lid 100 down to the microfluidic substrate 400 attached to the bottom surface of the middle piece 200. The hollow support pillar(s) 250 can though be used for more than providing visual inspection of the microfluidic substrate 400. In a particular embodiment, the top lid 100 and in particular the through hole(s) 130 aligned with the hollow support pillar(s) 250 is adapted to be connected to a vacuum pump. This vacuum pump will then apply a sucking pressure down to the microfluidic substrate 400 to thereby allow the bottom surface of the microfluidic substrate 400, i.e. the surface of the microfluidic substrate 400 that is opposite to the top surface that is attached to the bottom surface of the middle piece 200, to be reversibly attached to any flat support surface. In such a case, the microfluidic substrate 400 preferably comprises multiple circumferentially distributed vacuum channels around the central culture chamber. Such a microfluidic substrate 400 is described and disclosed in the international application WO 2010/056186. The sucking pressure developed by the vacuum pump may also be used to generally manipulate fluidic functions and samples in the microfluidic substrate 400 present in the microfluidic capsule 1.

This functionality of the microfluidic capsule 1 allows the upper unit with the top lid 100, the middle piece 200 and the microfluidic device 400 to reversibly bond the microfluidic substrate 400 to any surface of choice, including cover slips, Petri dishes, etc.

As was mentioned in the foregoing, the middle piece 200 preferably comprises multiple, i.e. at least two, support pillars 250. In such a case, the support pillars 250 are attached to the middle sheet 210 on either sides of the light window 220 and its circumferential or circumferentially distributed walls 240. It is generally, from stability point of view, preferred to have two support pillars 250 as illustrated in the figures. Increasing the number of support pillars 250 beyond two does not lead to that much gain in terms of stability but rather increases the complexity of the middle piece 200 and in particular the reduces the space available to the inlet connector 270, and any outlet connector and optional waste absorber 500.

The at least one fluid outlet 285 can be connected to at least one outlet connector. In such a case, the outlet connector is, for instance, in the form of a tube having a first end connected to the at least one fluid outlet 285 and having a second, opposite end protruding out through an opening of a wall of the multiple raised walls 230. Thus, the design of the at least one outlet connector could basically be equal to the design of the at least one inlet connector 270 as illustrated in the figures. The at least one outlet connector can then be connected to an external waste vessel or to an on-line detector or other equipment for analysis of waste fluid components.

In an alternative embodiment the microfluidic capsule 1 comprises no outlet connector. In clear contrast, waste or output fluid from the fluid channel(s) of the microfluidic substrate 400 enters the at least one fluid outlet 285 and thereby enters the space confined by the middle sheet 210, the lid sheet 110 and the multiple raised walls 230. In such a case, this space preferably comprises one or multiple waste absorbers 500. The waste absorber 500 is then designed to absorb any waste fluid coming from the at least one outlet 285 to thereby keep the waste fluid in the closed microfluidic capsule 1. Using such an integrated waste collection in the microfluidic capsule 1 will reduce the risk of fluid spill that might damage expensive microscopic equipment at which the microfluidic capsule 1 is arranged.

The waste absorber 500 is preferably designed to fit well inside the space and therefore has a design and shape that matches the one of the middle piece 200. For instance, the waste absorber 500 could be in a single piece having through hole(s) 510 through which the at least one support pillar 250 will extend when the waste absorber 500 is positioned in the middle piece 200. Additionally, through holes or an U-shaped hollow 520 of the waste absorber 500 lender space for the light window 220, the circumferential or circumferentially distributed walls 240, the fluid inlet(s) 280 and the inlet connector(s) 270. Another cavity or through hole 530 is preferably included in the waste absorber 500 to be positioned over the fluid outlet 585 to allow the waste fluid to enter and be absorbed by the waste absorber 500. Instead of having a waste absorber 500 as a single piece, multiple smaller waste absorbers can be positioned in different parts of the confined space.

The waste absorber 500 is manufactured in any fluid absorbent material and in particular made of a superabsorbent material, such as a superabsorbent polymer (SAP) material. Non-limiting examples include polyacrylate, polyacrylamide copolymer, ethylene maleic anhydride copolymer, cross-lined carboxymethylcellulose, polyvinyl alcohol copolymers, cross-linked polyethylene oxide, starch grafted copolymer of polyacrylonitrile. It is though generally sufficient if the waste absorber 500 can assimilate a few ml of fluid, such as about 5 ml of fluid, depending on the length of operation of the microfluidic capsule 1 and the input flow rate. For instance, a total input flow of 1 μl/min allows operation of the microfluidic capsule 1 for 3 days without exceeding the waste fluid assimilation capacity if the absorbent material can assimilate 5 ml of fluid.

The top lid 110 could then advantageously comprise at least one, two in the figures, observation windows 140 to allow visual access to the waste absorber 500 even when the top lid 100 is attached to the middle piece 200.

The at least one inlet connector 270 is preferably kept in place by at least one tube holder 275 arranged on the middle sheet 210. The tube holder 275 then locks the tube of the inlet connector 270 in correct position between the at least one fluid inlet 280 and the opening 272 in the wall. The tube holder 275 can be in the form of a structure having a U-shaped hollow or open channel in which the tube is running.

A corresponding tube holder could be arranged for locking a tube attached to the fluid outlet 285 in the case no waste absorber 500 is used and the waste fluid is instead led outside of the microfluidic capsule 1.

The end of the tube holder 275 opposite to the middle sheet 210 is preferably employed for attaching the top lid 100 to the middle piece 200, e.g. by gluing or welding, as is seen in FIG. 8.

The microfluidic substrate 400 constitutes, in a particular embodiment, a part of the microfluidic capsule 1. In such a case, the microfluidic substrate 400 is irreversibly or reversibly attached to the bottom surface of the middle sheet 210. Reversible attachment is possible if the microfluidic substrate 400 is made of an elastomer material simply by pushing the microfluidic substrate 400 to the bottom surface. Friction between the bottom surface of the middle sheet 210 and the microfluidic substrate 400 will lock the microfluidic substrate 400 to the bottom surface. Irreversible attachment can be realized by gluing the microfluidic substrate 400 to the middle sheet 210. Alternatively, the microfluidic substrate 400 can be attached to the middle sheet 210 by bonding to the bottom surface. Such irreversible attachment can be performed through surface modification of the microfluidic substrate 400 by exposure to air plasma to render the surface hydrophilic. The oxidized top surface then binds irreversibly to the middle sheet 210, in particular if the microfluidic substrate 400 is made of PDMS or another elastomer and the middle sheet 210 is a plastic material.

An example of a microfluidic substrate 400 that can be used in connection with the microfluidic capsule 1 is disclosed and described in WO 2010/056186, the teaching of which with regard to the design the microfluidic substrate is incorporated herein as reference.

The at least one fluid inlet 280 preferably comprises an inlet nipple per fluid inlet 280. The inlet nipple protrudes from the middle sheet 210 and down towards a respective inlet channel of the microfluidic substrate 400. Correspondingly, the at least one fluid outlet 285 preferably comprises an outlet nipple per fluid outlet 285. The outlet nipple protrudes from the middle sheet 210 and down towards a respective outlet channel of the microfluidic substrate 400. The inlet and outlet nipples thereby provide an efficient fluid connection between the microfluidic substrate 400 and the fluid inlet(s) 280 and fluid outlet(s) 285 and reduce the risk of fluid leakages. These inlet and outlet nipples further help locking the microfluidic substrate 400 in correct position relative the middle sheet 210.

The design and shape of the top lid 100, middle piece 200 and bottom piece 300 of the microfluidic capsule 1 are preferably selected to match the corresponding size and shape of the microfluidic substrate 400 to be enclosed in the microfluidic capsule 1. For instance, the overall shape of the microfluidic capsule 1 could be circular, elliptical, quadratic or rectangular. The size, such as diameter, of the microfluidic capsule 1 is generally from one or a few centimeters up to several, such as up to five or ten centimeters, though depending on the particular microfluidic substrate 400.

The top lid 100, middle piece 200 and the bottom piece 300 are advantageously manufactured from plastic material and are preferably all manufactured from the same plastic material. Preferred such plastic materials include thermoplastic materials, such as selected from the group of polystyrene, cycloolefine polymer and polycarbonate.

The transparent cover sheet 340 can be made from various optically transparent materials, such as borosilicate glass or plastic materials.

With the above listed material examples the microfluidic capsule 1 is advantageously in the form of a disposable plastic capsule 1 that facilitates the operation of diverse microfluidic substrates 400. Notably, there are preferably no metal parts in the microfluidic capsule 1. The microfluidic capsule 1 can then be uniquely designed to be produced in thermoplastics by injection molding. A microfluidic substrate 400, and a cover slip or sheet 340 is inserted into the space between middle piece 200 and bottom piece 300 to make the capsule 1 operational.

Measures were taken during the design and construction of the microfluidic capsule 1 to counteract tension-related structural deformations in the three different main parts, termed top lid 100, middle piece 200 and bottom piece 300. Mechanical stress was uniquely identified by FEM modeling. The walls 240 and support pillars 250 of the middle piece 200 together with the top lid 100 additionally contributed to make the capsule 1 mechanically robust and to considerably enhance the stiffness of the flat middle piece bottom surface without the need for making it thicker. Specifically, the support pillars 250 provide additional structural stability to the microfluidic capsule 1 and help smoothing the pressure from the snap fits over the surface.

The top lid 100 is preferably bonded (glued or ultrasonically welded) permanently with the middle piece 200 and the bonding of the two pieces stabilizes the middle piece 200 and this efficiently counteracts deformation of the middle piece 200 upon snapping the bottom piece 300 to the middle piece 200 in the upper unit during final capsule assembly.

The light windows 120, 220, 320 enable light microscopy where the light must fall through the sample placed in the culture chamber of the microfluidic substrate 400. The light window 220 with its wall(s) is additionally designed to enhance the resistance against the pressure formed by closing of the snap-fits. The light windows 120 and 220 further enables parts of the top surface of the microfluidic substrate 400 to be exposed to atmosphere which ensures gas exchange in the fluidic structures in the microfluidic substrate 400 given that the elastomer material of the microfluidic substrate 400 is gas permeable.

The design and geometrical shape of the microfluidic capsule 1 uniquely allows it to be operated in both upright and inverted modes, and the capsule 1 is thus compatible with live imaging of samples in all types of microscope setups, e.g. both in inverted and in upright microscopes. The functionalities of the capsule 1, such as clamping and operation of microfluidic substrate 400, waste collection, microscopic analyses, connections to external pumps, etc., are not changed by operation of microfluidic capsule 1 in either upright or inverted mode.

The capsule 1 allows for the operation of a variety of microfluidic substrates 400, allowing management of advanced two- or three-dimensional organ/cell culture models, to study effects on cell behavior using for example live microscopy. The capsule 1 also enables biochemical interaction studies in real time by operation of suitable microfluidic substrates 400.

It is possible to perform live-imaging and associated data collection during the full course of an experiment, due to the sample visibility through the bottom piece 300 and the cover sheet 340, and due to the light windows 120, 220 for light microscopy that goes through the top lid 100 and middle piece 200 of the capsule 1.

The microfluidic capsule 1 can be opened and closed as many times as required, by the locking or unlocking of the integrated snap-fits, prior to, during or after a completed experiment.

The microfluidic capsule 1 preferably has an integrated macro-to-micro interface that is used to connect an external perfusion system (pump) to a microfluidic substrate 400 of preferably polydimethylsiloxane material. The perfusion system is connected via tubing to the inlet nipples. The nipples direct the fluid through the middle piece 200 of the capsule 1 into channels that are cast into the microfluidic substrate 400. Nipples on the bottom surface of the middle piece 200 are also used to align the microfluidic substrate 400 with the middle piece 200 during the assembly process.

The microfluidic capsule 1 preferably has an integrated capacity to absorb waste from the fluidic system, using a waste-assimilating super-absorbent placed in the waste-collection compartment in direct contact with the outlet nipple. The waste-collection compartment can be filled with any type of absorbent material, but can also collect fluid in the absence of absorbent. The outlet nipple can alternatively be connected to tubing that lead to any type of optional vessel outside of the microfluidic capsule 1, or alternatively can be connected to any type of on-line detector for direct analysis of the exudates.

The bottom piece 300 of the microfluidic capsule 1 can be loaded with any type of cover slip or sheet 340. However, for most applications where a microscope will be used to analyze reactions in the fluidic system using microscopy, a planar cover slip of glass or optically transparent plastic material will be optimal.

The capsule outlet can be connected to any type of on-line detector system, to detect factors/proteins produced by the biological samples or from biochemical reactions in the microfluidic substrate 400, or to detect consumption of any type of molecule that can be detected by an on-line detector.

The microfluidic capsule 1 enables a mechanical and non-covalent bonding of a microfluidic substrate 400 to a cover slip of choice for closure of fluidic channels to functionally activate the fluidic functions of any type of microfluidic substrates 400. The closure of the microfluidic capsule 1 is based on the use of integrated plastic snap-fits positioned at regular or irregular intervals along the device perimeter in the bottom piece 300. Cavities for the snap-fits are provided in the middle piece 200.

The design and size of the microfluidic capsule 1 can easily be changed to fit specific experimental requirements. For example, the number and position of inlet and/or outlet nipples can be increased or decreased. Further, the number of snap-fits can be increased and the locations of the snap-fits altered along the circumference of the microfluidic capsule 1.

The microfluidic capsule 1 makes it possible for individuals with no expertise in engineering to operate a variety of microfluidic substrates 400, to perform cell assays to study the behavior of cells in response to artificially created stimuli, such as concentration gradients, beams of molecular factors, fluid flow related shear stress, levels of gases and oxygen, levels of temperature, to control the levels of any molecular substance in a given fluidic compartment or void connected to a fluidic structure, and to study the biochemical properties of these substances and their biochemical interactions.

The microfluidic capsule 1 can be used to operate fluidic systems to, for example, create molecular gradients to affect and direct complex biological processes in biological material such as cells and clusters of cells and small organisms.

The microfluidic substrates 400 will provide different functionalities to, for example, create complex gradient shapes, or beams of factors/chemical compounds/reagents/tracers, in the culture chamber or connected to the inlet or outlet channels, to enable better detection of biological processes.

The microfluidic capsule 1 can be used to operate microfluidic substrates 400 to determine effective or lethal doses for any soluble compound that can be used to create a gradient in the device, by analyzing concentration-dependent effects on cells that are in the microfluidic substrate 400. The microfluidic capsule 1 will thus enable the use of microfluidic assays to screen for the biological activities of pharmacological compounds or for the testing of new drugs.

The assembled microfluidic capsule 1 can be used to study multiple gradients or beams of stimulatory factors (including gases) of different shape and their simultaneous effects on all types of cell. Both activators and inhibitors (agonists, antagonists) can be studied in the microfluidic capsule 1.

The microfluidic capsule 1 is especially well suited for operation of microfluidic substrates 400 that enable studies of angiogenesis and nerve cell formation, communication and growth, studies of tumor cells, and tumor/cancer material isolated from patients. The effects of different compounds on cancer cells can be studied live due to the availability of using microscope or other type of data collection through the bottom plate; drug screening, toxicity tests, diagnostic tests to identify different disease types or the stage/progression of a disease, early testing of new treatments on tumor cells, normal tissue and blood vessels.

After a completed experiment, the intact sample(s) can be retrieved from the microfluidic substrate 400, using forceps/scalpel or by adding enzymes to release sample, such as cells or molecules, attached to the microfluidic substrate 400, followed by sample retrieval by, for instance, liquid flushing. Any type of analysis of the retrieved sample is then possible. For example, fixation and immunohistochemical analysis of the sample, dissociation of the gel and isolation of material for cell sorting (FACS), isolation of cells, isolation of cells and mRNA for PCR, isolation of cells and proteins for western blotting, etc.

The biological material can also be retrieved from the microfluidic substrate 400 for further culture and experimentation in other cell culture systems, or for injection into laboratory animals for further experimentation.

EXPERIMENTS

Complete microfluidic capsules were produced by 3D printing in DurusWhite. Proof-of-concept tests were performed using a previously published PDMS substrate, see WO 2010/056186, for concentration gradient formation through a 3D culture chamber, here filled with different types of cell matrices (collagen I, Matrigel and fibrin). Circular cover slips in borosilicate glass (0.3 mm thick; Thermo Fisher Scientific) were used as bottom substrates within the capsule. Testing showed that the present capsule tolerated PDMS substrates having a thickness of 2.70-2.95 mm for maintained functionality. With this set-up, there were no detectable leakages in any part of the system. Primary endothelial cells (HMVEC, PromoCell) were grown for up to three days in the capsule using standard endothelial cell culture conditions. The cells proliferated and migrated; no signs of elevated apoptosis could be detected. FIGS. 9A and 9B illustrate primary human endothelial cells seeded in collagen-I matrix in the centrally located cell culture chamber of the PDMS substrate. After matrix polymerization, the microfluidic capsule was closed and medium flowed through the system at a rate of 0.5 μl/min. The cells were monitored over time and shown to be viable and migrating after 60 hours of culture in the closed capsule. Scale bar=100 μm.

Concentration gradients of molecules could readily be formed in the closed microfluidic capsule connected to a syringe pump (Harvard Apparatus). The gradients were directly comparable to our previously published results, see Barkefors et al, *Lab Chip*, 2009, 9: 529-535. FIG. 10 is a diagram showing the formation of a FITC-dextran (MW=40 kDa, Sigma Aldrich) concentration gradient in the 4 mm wide culture chamber of the PDMS substrate filled with fibrin gel.

Figure 11A:
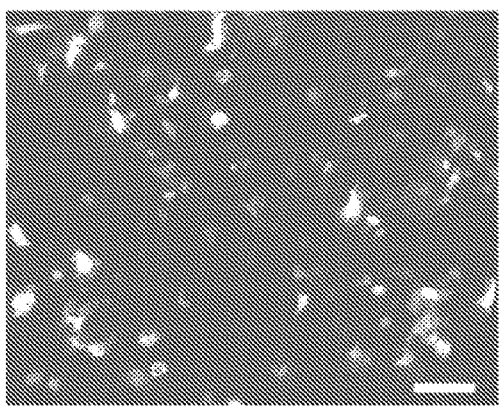
FIGS. 11A and 11B illustrate a comparison of fluorescent signals emitted from endothelial cells expressing GFP in collagen-I matrices grown either in an assembled microfluidic capsule according to an embodiment fitted with a microfluidic substrate (FIG. 11B) or in an equal volume of collagen-I gel directly placed on a cover glass (FIG. 11A).
Figure 11B:
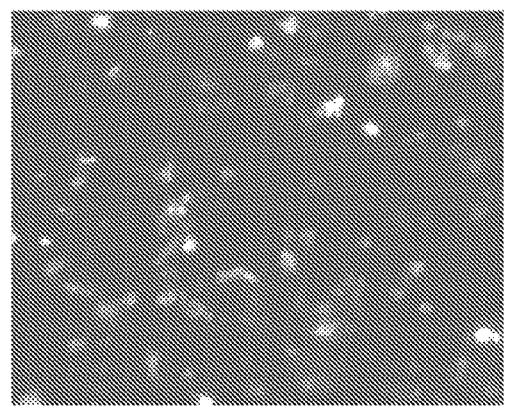

Endothelial cells transfected with a GFP expression plasmid (pmaxGFP, Lonza) were used to measure GFP-signal reduction as a result of encapsulation. It was found that the signal intensity from cells in the microfluidic capsule was moderately weaker as compared to cells deposited in a gel directly placed onto a cover slip, FIGS. 11A and 11B. Images were acquired using an inverted Zeiss Axiovert 200 microscope, equipped with an AxioCam MRm camera (Zeiss) and Zeiss Axiovision imaging software. FIGS. 11A and 11B illustrate a comparison of fluorescent signals emitted from endothelial cells expressing GFP in collagen-I matrices, grown either in the assembled microfluidic capsule (FIG. 11B, mean intensity of complete image=19.2 A.U.) or in an equal volume of collagen-I gel directly placed on a cover glass (FIG. 11A, mean intensity of complete image=22.1 A.U.). Scale bar=100 μm.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A microfluidic capsule comprising:
   a top lid in the form of a lid sheet comprising a light window;
   a middle piece comprising:
      a middle sheet having a perimeter and comprising at least one fluid inlet and at least one fluid outlet in the form of through holes in said middle sheet and a light window positioned to be aligned with said light window of said top lid when said top lid is attached to said middle piece and having a circumferential or circumferentially distributed wall around its perimeter;
      multiple raised walls circumferentially distributed around said perimeter of said middle sheet and separated by raised connection structures having a height relative said middle sheet that is lower than a height of said multiple raised walls relative said middle sheet;
      at least one support pillar attached to said middle sheet at a position between said perimeter of said middle sheet and said perimeter of said light window of said middle piece, wherein the ends of said multiple raised walls said circumferential or circumferentially distributed wall and said at least one support pillar facing opposite to said middle sheet are arranged to be attached to said top lid; and
      at least one inlet connector in the form of a tube having a first end connected to said at least one fluid inlet and having a second, opposite end protruding out through an opening of a wall of said multiple raised walls; and
   a bottom piece comprising:
      a bottom sheet having a perimeter and a light window allowing visual inspection through said light window of said bottom piece, said light window of said top lid and said light window of said middle piece when said bottom piece is attached to said middle piece and said top lid;
      multiple snap-fit structures circumferentially distributed around said perimeter of said bottom sheet and extending from said bottom sheet and positioned to be aligned with said raised connection structures to lock said bottom piece to said middle piece; and
      a transparent cover sheet, wherein said microfluidic capsule is designed to enclose a microfluidic substrate between said bottom piece and said middle piece so that an open culture chamber of said microfluidic substrate aligned with said light windows of said top lid, said middle piece and said bottom piece becomes closed by said transparent cover sheet and at least one fluid channel of said microfluidic substrate (400) becomes connected to said at least one fluid inlet and said at least one fluid outlet.

2. The microfluidic capsule according to claim 1, wherein said at least one support pillar is at least one hollow support pillar having a bore and said top lid comprises at least one through hole positioned in said lid sheet to be aligned with said bore when said top lid is attached to said middle piece and adapted to be connected to a vacuum pump to apply a sucking pressure between said microfluidic substrate and a support surface to reversibly attach said microfluidic substrate to said support surface.

3. The microfluidic capsule according to claim 1, wherein said middle piece comprises two support pillars attached to said middle sheet on either sides of said light window of said middle piece.

4. The microfluidic capsule according to claim 1, wherein said lid sheet, said middle sheet and said bottom sheet are disc-shaped and said middle piece comprises three raised walls circumferentially distributed around said perimeter of said middle sheet so that each of said three raised walls covers substantially a same portion of said perimeter of said middle sheet as the other two of said three raised walls.

5. The microfluidic capsule according to claim 1, further comprising a waste absorber positioned in the space confined by said middle sheet, said lid sheet and said multiple raised walls and designed to absorb fluid entering said space from said at least one fluid outlet.

6. The microfluidic capsule according to claim 5, wherein said top lid comprises at least one observation window to allow visual access to said waste absorber in said space.

7. The microfluidic capsule according to claim 1, wherein said middle piece comprises at least one tube holder arranged on said middle sheet to lock said tube in position between said at least one fluid inlet and said opening of said wall, wherein the ends of said multiple raised walls, said circumferential or circumferentially distributed wall, said at least one support pillar and said tube holder facing opposite to said middle sheet are arranged to be attached to said top lid.

8. The microfluidic capsule according to claim 1, wherein said top lid is irreversibly attached to said middle piece via gluing or welding provided between said ends of said multiple raised walls, said circumferential or circumferentially distributed wall and said at least one support pillar and said lid sheet.

9. The microfluidic capsule according to any claim 1, wherein said light windows are respective through holes in said lid sheet, said middle sheet and said bottom sheet.

10. The microfluidic capsule according to claims 1, further comprising said microfluidic substrate irreversibly or reversibly attached to said middle sheet.

11. The microfluidic capsule according to according to claim 10, wherein said microfluidic substrate is made of an elastomer material.

12. The microfluidic capsule according to claim 1, wherein said at least one fluid inlet comprises at least one inlet nipple protruding from said middle sheet and said at least one fluid outlet comprises at least one outlet nipple protruding from said middle sheet), wherein said at least one inlet nipple and said at least one outlet nipple are designed to enter said at least one fluid channel.

13. The microfluidic capsule according to claim 1, wherein said lid sheet, said middle sheet and said bottom sheet are made of a thermoplastic material selected from the group consisting of polystyrene, cycloolefine polymer and polycarbonate.

14. The microfluidic capsule according to claim 1, wherein said transparent cover sheet is made of an optically transparent material.

15. The microfluidic capsule according to claim 14 wherein said optically transparent material is borosilicate glass.

16. The microfluidic capsule according to according to claim 11, wherein said elastomer material is polydimethylsiloxane.

\* \* \* \* \*

UNITED STATES PATENT AND TRADEMARK OFFICE
CERTIFICATE OF CORRECTION

PATENT NO. : 8,828,332 B2
APPLICATION NO. : 13/821293
DATED : September 9, 2014
INVENTOR(S) : Sara Thorslund et al.

It is certified that error appears in the above-identified patent and that said Letters Patent is hereby corrected as shown below:

In the Claims

Claim 1, Column 14, Line 20, delete "(400)".

Claim 10, Column 15, Line 1, change "claims" to --claim--.

Claim 12, Column 15, Line 11, change "sheet)," to --sheet,--.

Signed and Sealed this
Twenty-fourth Day of February, 2015

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,828,332 B2 | Page 1 of 1 |
| APPLICATION NO. | : 13/821293 | |
| DATED | : September 9, 2014 | |
| INVENTOR(S) | : Thorslund et al. | |

It is certified that error appears in the above-identified patent and that said Letters Patent is hereby corrected as shown below:

In the Claims

Claim 1, Column 13, Line 59, after "raised walls", add --,--.

Signed and Sealed this
Eighth Day of September, 2015

Michelle K. Lee
*Director of the United States Patent and Trademark Office*